United States Patent
Koo et al.

(10) Patent No.: US 11,746,547 B2
(45) Date of Patent: Sep. 5, 2023

(54) SMART TUNNEL HAVING REGULAR QUARANTINE AND DISINFECTION FUNCTION FOR PREVENTING PROLIFERATION OF INFECTIOUS DISEASE

(71) Applicant: KOREA INSTITUTE OF CIVIL ENGINEERING AND BUILDING TECHNOLOGY, Goyang-si (KR)

(72) Inventors: Hyun-Bon Koo, Goyang-si (KR); Jung-Jun Park, Paju-si (KR); Jong-Won Kwark, Goyang-si (KR); Im-Jong Kwahk, Paju-si (KR); Seong-Jun Kim, Goyang-si (KR)

(73) Assignee: KOREA INSTITUTE OF CIVIL ENGINEERING AND BUILDING TECHNOLOGY, Goyang-si (KR)

(*) Notice: Subject to any disclaimer, the term of this patent is extended or adjusted under 35 U.S.C. 154(b) by 360 days.

(21) Appl. No.: 17/288,943

(22) PCT Filed: Oct. 28, 2019

(86) PCT No.: PCT/KR2019/014240
§ 371 (c)(1),
(2) Date: Apr. 27, 2021

(87) PCT Pub. No.: WO2020/091327
PCT Pub. Date: May 7, 2020

(65) Prior Publication Data
US 2021/0381264 A1    Dec. 9, 2021

(30) Foreign Application Priority Data
Oct. 29, 2018 (KR) .................. 10-2018-0129996

(51) Int. Cl.
*A61L 9/00* (2006.01)
*E04H 1/12* (2006.01)
(Continued)

(52) U.S. Cl.
CPC .......... *E04H 1/1277* (2013.01); *A61B 5/1176* (2013.01); *A61L 9/00* (2013.01);
(Continued)

(58) Field of Classification Search
CPC .......... A61L 9/00; E04H 1/1277; G16H 50/30
See application file for complete search history.

(56) References Cited

U.S. PATENT DOCUMENTS

2012/0251388 A1* 10/2012 Case, III ................. B60P 3/005
422/119

FOREIGN PATENT DOCUMENTS

| JP | 2012-052865 A | 3/2012 |
| KR | 10-1297693 B1 | 8/2013 |

(Continued)

OTHER PUBLICATIONS

1. KRICT's blog, <https://blog.naver.com/krictblog/220907422581>, "Making a diagnosis of new virus can be confirmed in 10 minutes,", Jan. 10, 2017.

*Primary Examiner* — Kevin Joyner
(74) *Attorney, Agent, or Firm* — GOLDILOCKS ZONE IP LAW

(57) ABSTRACT

The present disclosure relates to a smart tunnel having a tunnel structure having a quarantine section and a disinfection section, which is capable of regularly performing a quarantine function for determining whether an infectious disease is introduced and a disinfection function for preventing spread of an infectious disease.

5 Claims, 10 Drawing Sheets

(51) Int. Cl.
   *G16H 50/30* (2018.01)
   *G16H 50/80* (2018.01)
   *A61B 5/1171* (2016.01)
   *G06V 40/20* (2022.01)
   *G06V 40/16* (2022.01)
   *F24F 8/20* (2021.01)

(52) U.S. Cl.
   CPC ............ *G06V 40/166* (2022.01); *G06V 40/20* (2022.01); *G16H 50/30* (2018.01); *G16H 50/80* (2018.01); *A61L 2209/16* (2013.01); *F24F 8/20* (2021.01)

(56) References Cited

FOREIGN PATENT DOCUMENTS

| | | |
|---|---|---|
| KR | 10-2017-0011266 A | 2/2017 |
| KR | 10-1806400 B1 | 1/2018 |
| KR | 10-2018-0098963 A | 9/2018 |

\* cited by examiner

SMART TUNNEL HAVING REGULAR QUARANTINE AND DISINFECTION FUNCTION FOR PREVENTING PROLIFERATION OF INFECTIOUS DISEASE

CROSS REFERENCE TO RELATED PATENT APPLICATIONS

This application claims the benefit under 35 U.S.C. Section 371, of PCT International Application No. PCT/KR2019/014240, filed Oct. 28, 2019, which claimed priority to Korean Patent Application No. KR 10-2018-0129996, filed Oct. 29, 2018, the disclosures of which are hereby incorporated by the references.

TECHNICAL FIELD

This disclosure relates to a smart tunnel having a quarantine function for determining whether a person passing through a tunnel structure is infected by using an image of the person and a disinfection function for suppressing spread of an infectious disease.

The present disclosure is supported by the National Research Council of Science & Technology (NST) grant by the Korea government (MSIT), titled "Development of convergent solution for emerging virus infection (project name: Development of smart construction materials and tunnels to prevent the spread of an infectious disease), among the future-leading convergence research group projects of the Ministry of Science and ICT (MSIT) (Project No.: CRC-16-01-KRICT) (Project Research Period: Aug. 1, 2017 to Jul. 31, 2018)".

BACKGROUND ART

Various foreign infectious diseases are introduced and spread into the country due to inbound passengers who enter the country from abroad through immigration facilities such as airports and ports. In addition, in hospitals, infectious diseases are often proliferated to third parties due to direct or indirect contact with an infected person. In order to prevent the spread of foreign infectious diseases from entering the country through entrants from abroad, conventionally, a simple thermal imaging camera for detecting the fever of an inbound passenger is installed at the immigration facility to monitor the entry of an infected person through thermal imaging.

However, it takes a long time to determine whether an inbound passenger is infected, and after the inbound passenger is determined as an infected person, it takes a considerable amount of time to track and quarantine the infected person, which makes it difficult to prevent the spread of infectious diseases. In addition, since the space where the infected person has passed is not disinfected immediately, non-infected persons pass without protection through the space where the infected person has passed, and thus there is a very high concern about the occurrence of additional infected persons and the spread of infectious diseases.

DISCLOSURE

Technical Problem

This disclosure is directed to providing a technology, which allows to manage (measures such as tracking, finding-out, and quarantine) of an infected person or persons exposed to infection risk through direct or indirect contact with the infected person and to make rapid and appropriate initial countermeasures against the introduction of infectious diseases by rapidly determining whether an infected person appears and whether an infectious disease is introduced at immigration facilities such as airports and ports and crowded facilities such as hospitals where management is required for blocking the introduction of infectious disease and preventing the spreading and providing relevant information to a management entity.

The present disclosure is directed to providing a technology, which may suppress the spread of infectious diseases by reducing the infection risk of non-infected persons who share the same time and space as an infected person.

Technical Solution

The present disclosure provides a smart tunnel, which includes a tunnel structure having a quarantine section and a disinfection section, which is capable of regularly performing a quarantine function and a disinfection function.

Advantageous Effects

According to the present disclosure, it is determined whether an infectious disease is introduced while a passenger is passing through the tunnel structure, and the information of the passenger who is determined as an infected person and persons (infection-suspected candidate group) exposed to the infection risk by sharing the same time and space as the infected person may be quickly figured out. Therefore, if the present disclosure is used, effective measures to prevent the spread of the infectious disease may be quickly devised by taking quick management measures for the infected person and the infection-suspected candidate group.

Since the smart tunnel according to the present disclosure has a tunnel structure, it has an advantage of effectively controlling moving lines of infection-suspected persons or infection-suspected crowd.

The smart tunnel according to the present disclosure may effectively sterilize and purify the pathogen that may exist in the tunnel structure due to breathing, cough, or the like of the infected person, thereby suppressing the spread of the infectious disease.

BEST MODE

The present disclosure provides a smart tunnel in which a <quarantine section> having a plurality of tunnel structures through which one passenger passes and a <disinfection section> having a tunnel structure connected to all or a part of the plurality of quarantine section tunnel modules so that passengers passing through the <quarantine section> pass together are formed sequentially in a longitudinal direction along which the passengers move.

In the smart tunnel of the present disclosure, in the quarantine section tunnel module, an "intelligent infected person regular detection system" for sensing an abnormal state (fever, or the like) and an abnormal behavior (cough, collapse, abnormal walking, or the like) of the passenger through a thermal image and a visible light image to determine an infection-suspected person and recognizing and detecting a face or the like of the passenger determined as an infection-suspected person is provided.

In the quarantine section tunnel module, an "infected person integrated control system" for collecting and managing identity information transmitted from the intelligent infected person regular detection system, securing identity information of the infection-suspected person (if necessary, including a person or crowd (infection-suspected candidate group) in direct or indirect contact with the infection-suspected person), and alarming and notifying the presence of the infection-suspected person and relevant information (abnormal state and behavior, face and identity information) of the infection-suspected person to a manager is provided.

In the quarantine section tunnel module, a "pathogen capturing system" for sucking the air in the tunnel structure to capture (separate and concentrate) a pathogen (bacteria, virus, etc.) discharged into the air by breathing, cough or the like of an infected person and measuring the type and quantity of the pathogen is provided.

In the disinfection section tunnel module, a finishing material having antibacterial and antiviral performance is applied to members and facilities in the tunnel structure, and an air conditioning system having antibacterial and antiviral performance is installed. In the disinfection section tunnel module, a pathogen (bacteria, virus, etc.) discharged from an infected person into the air is killed when contacting the applied finishing material or passing through the installed air conditioning system.

MODE FOR INVENTION

When explaining the present disclosure, a direction along which passengers pass will be referred to as a "longitudinal direction" and a direction orthogonal thereto on the horizontal plane will be referred to as a "lateral direction".

Figure 1:
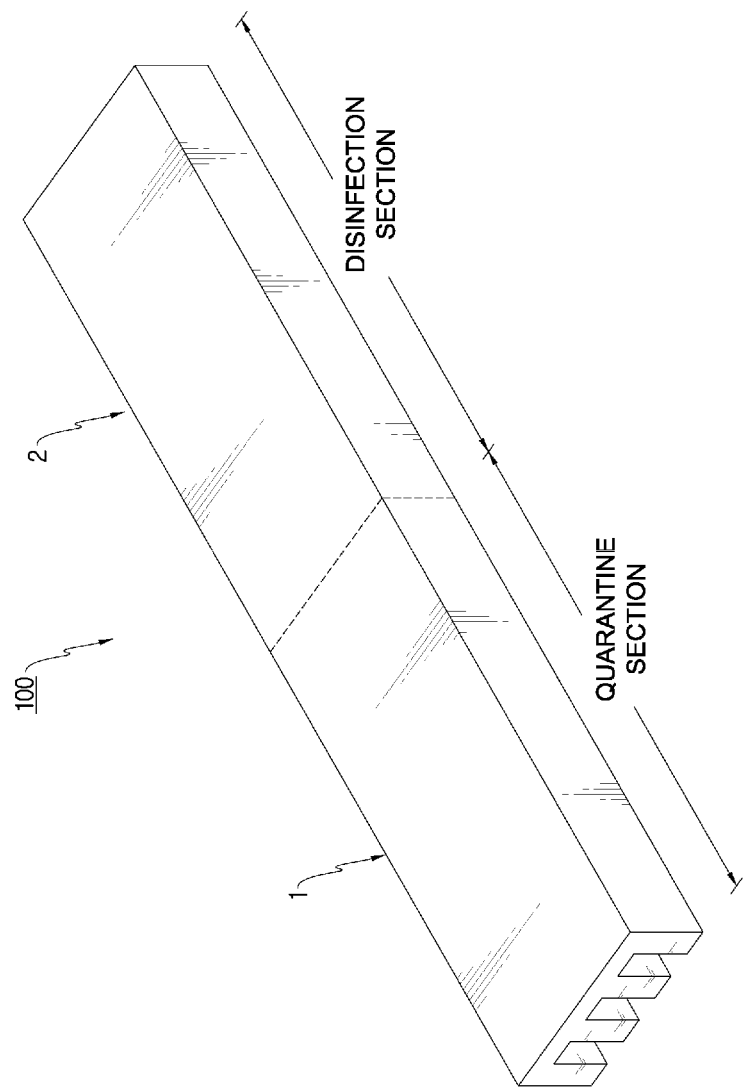
FIG. 1 is a schematic perspective view showing a smart tunnel according to an embodiment of the present disclosure.
Figure 2:
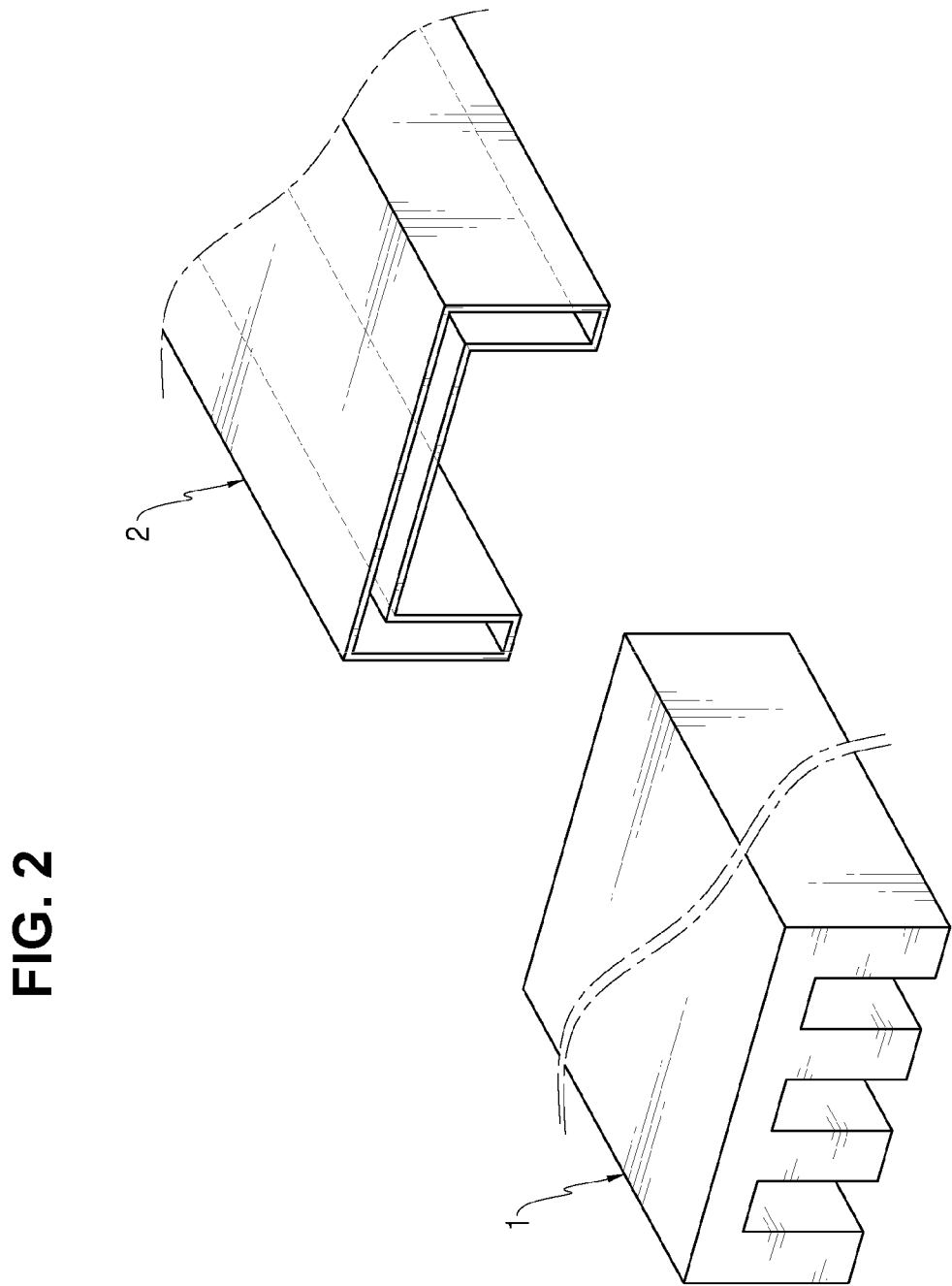
FIGS. 2 and 3 are schematic perspective views showing that a <quarantine section> and a <disinfection section> of the smart tunnel of the present disclosure depicted in FIG. 1 are in a separated state.
Figure 3:
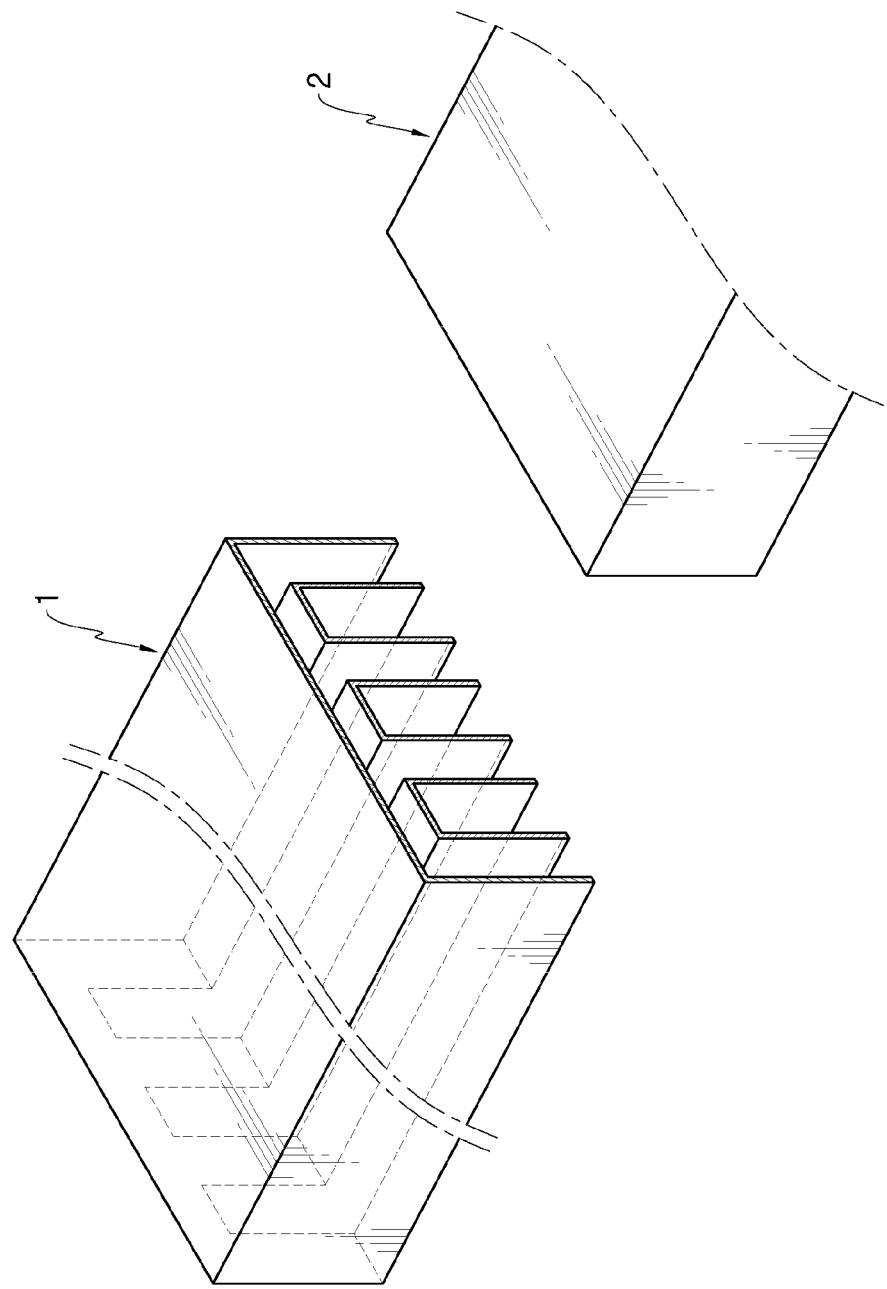

FIG. 1 is a schematic perspective view showing a smart tunnel 100 according to an embodiment of the present disclosure. The smart tunnel 100 of the present disclosure is divided into a quarantine section and a disinfection section along a longitudinal direction. A section of a predetermined length from the entrance where a passenger enters the smart tunnel 100 becomes the quarantine section. A section from the quarantine section to the exit of the smart tunnel 100 becomes the disinfection section. FIGS. 2 and 3 are schematic perspective views showing the quarantine section and the disinfection section constituting the smart tunnel 100 of the present disclosure.

In the smart tunnel 100, the quarantine section is configured to include a plurality of quarantine section tunnel modules 1 through each of which one passenger passes. In each quarantine section tunnel module 1, an "infection suspicion determining work" is performed based on an abnormal state (fever, etc.) and abnormal behavior (cough, collapse, abnormal walking, etc.) of the passenger while the passenger is passing through the quarantine section tunnel module 1. In addition, while the passenger is passing through the quarantine section tunnel module 1, a "pathogen capturing work" is performed to capture a pathogen such as bacteria and virus discharged from the infected person. The disinfection section is connected to all or a part of the plurality of quarantine section tunnel modules 1 so that passengers passing through the quarantine section tunnel modules 1 passes together. The disinfection section includes materials having antibacterial and antiviral performance and an air conditioning system having antibacterial and antiviral performance. Therefore, in the disinfection section, members and facilities inside the tunnel structure and the air in the tunnel structure are sterilized and purified.

The smart tunnel 100 includes an "intelligent infected person regular detection system". The intelligent infected person regular detection system determines whether a passenger is an infection-suspected person by using a thermal image and a visible light image thereof, and recognizes and detects a face or the like of the person identified as an infection-suspected person. The smart tunnel 100 includes an "infected person integrated control system". The infected person integrated control system receives information transmitted from the intelligent infected person regular detection system. The infected person integrated control system secures identity information of the infection-suspected person and transmits the presence of the infection-suspected person and information related to the infection-suspected person (information about an abnormal state and an abnormal behavior, face and identity information) to a management terminal of the manager such as a smartphone, a tablet and a personal computer in real time. The smart tunnel 100 includes a "pathogen capturing system". The pathogen capturing system captures a pathogen discharged by breathing, cough, or the like of an infected person and measures the type and amount thereof to determine whether an infectious disease is introduced, and determine the type of the introduced infectious disease.

Figure 4:
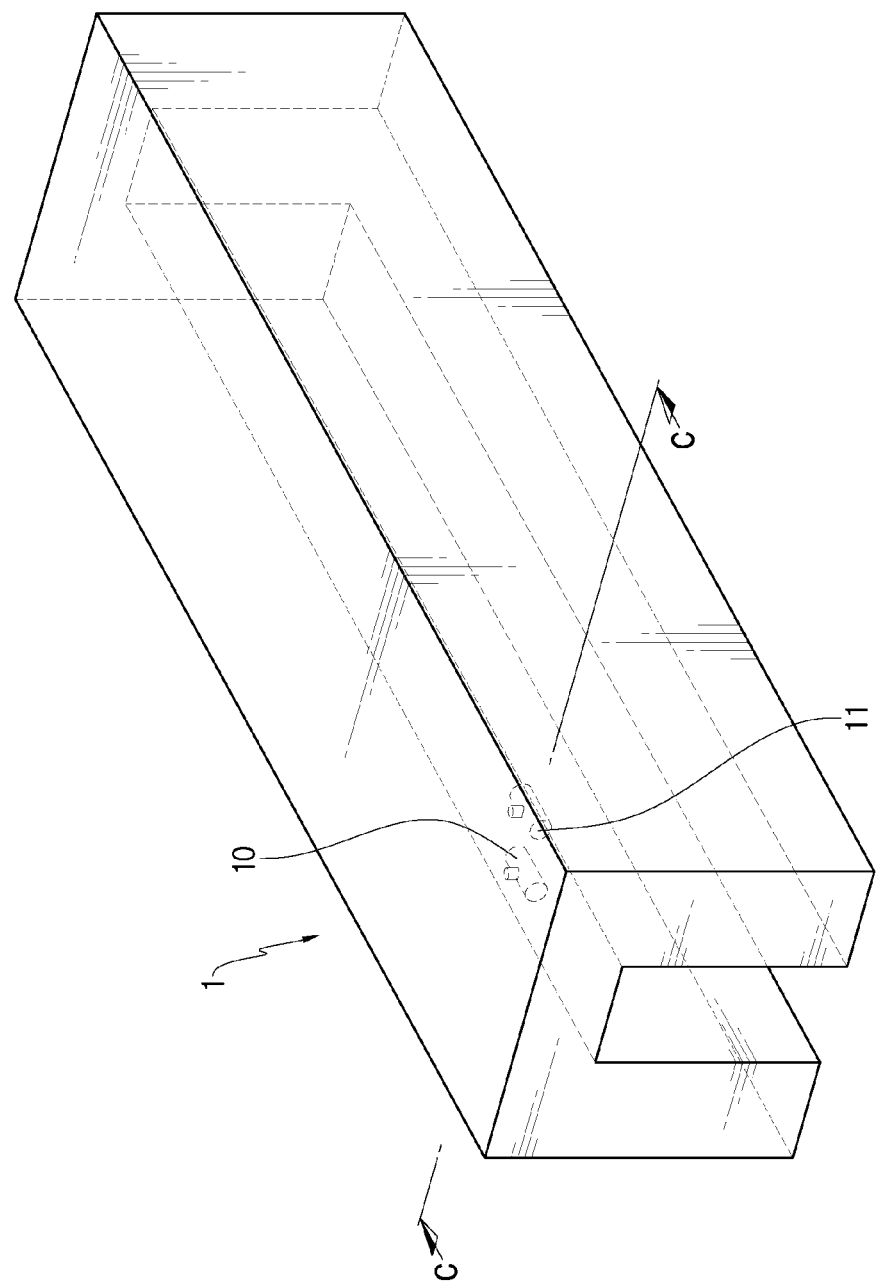
FIG. 4 is a schematic perspective view showing an embodiment of a tunnel structure, which forms a quarantine section tunnel module in the smart tunnel of FIG. 1.
Figure 5:
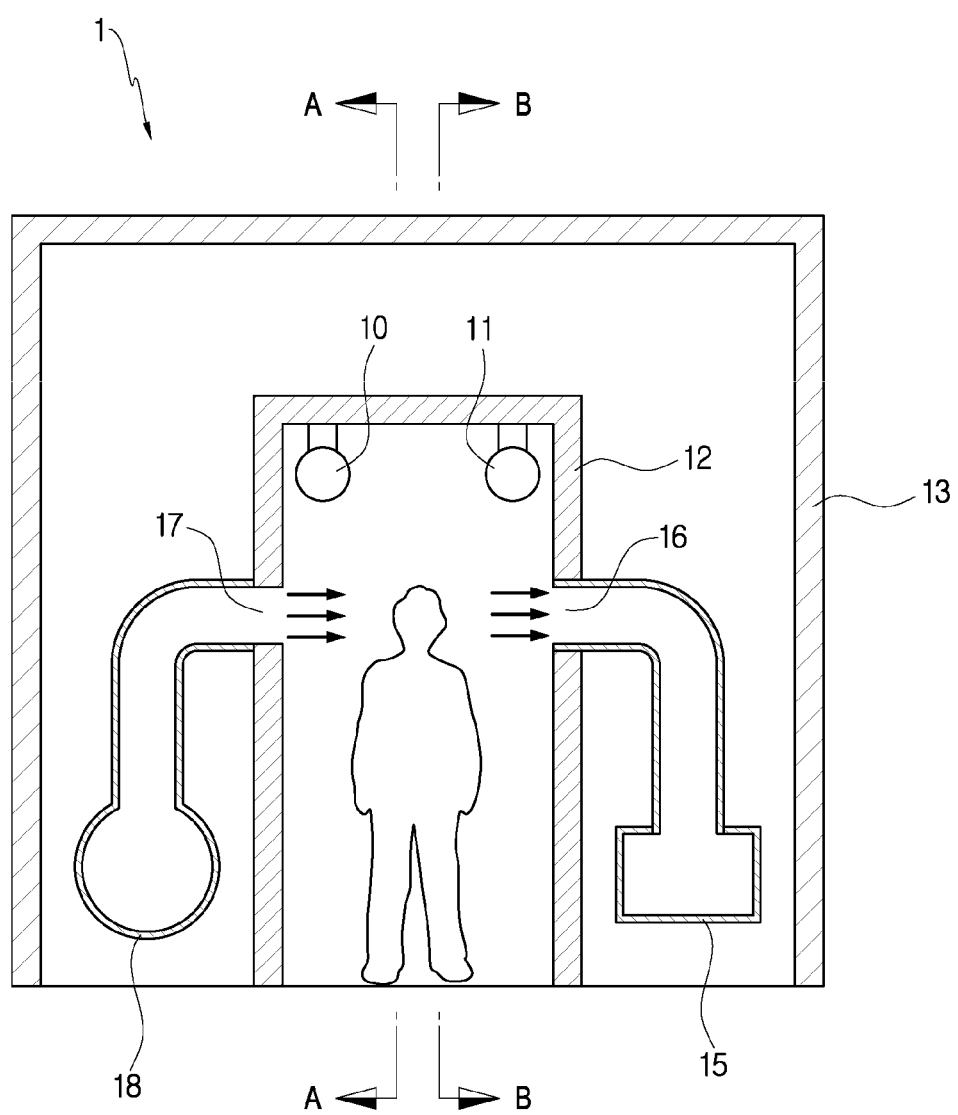
FIG. 5 is a schematic longitudinal sectional view showing the quarantine section tunnel module, taken along the arrow C-C of FIG. 4.
Figure 6:
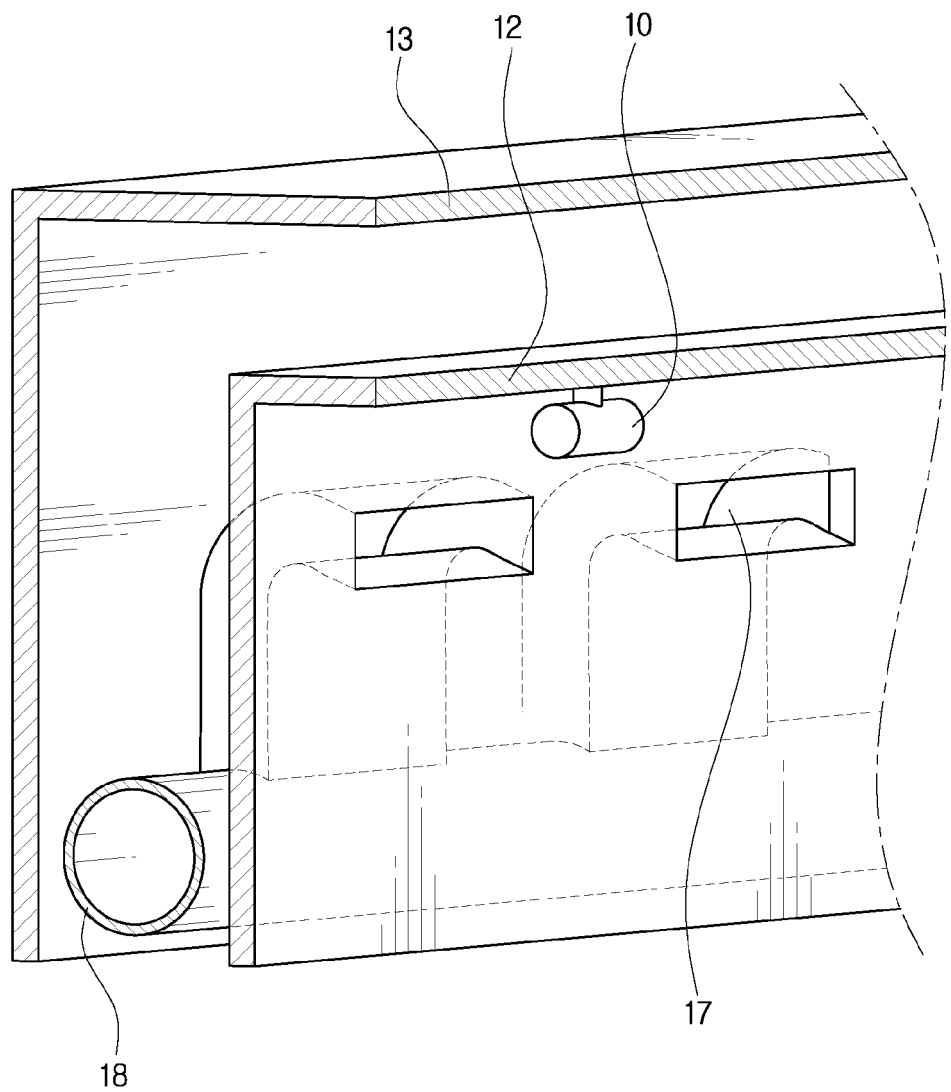
FIG. 6 is a schematic lateral half-sectional view, taken along the arrow A-A of FIG. 5.
Figure 7:
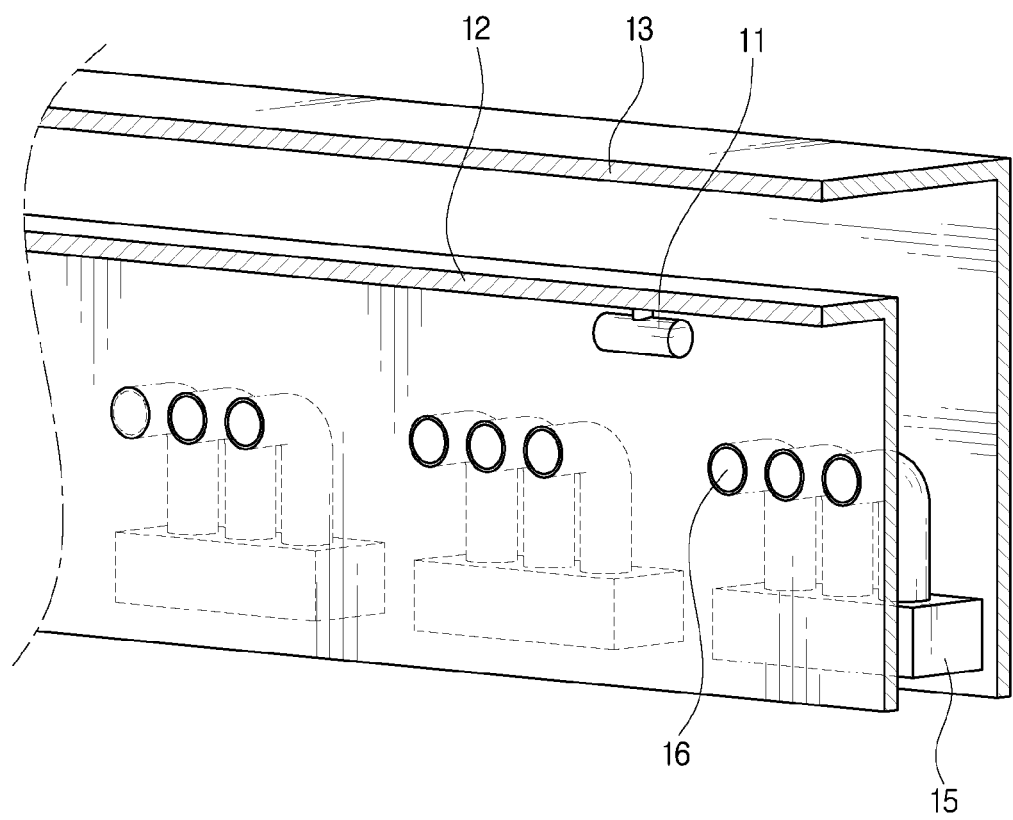
FIG. 7 is a schematic lateral half-sectional view, taken along the arrow B-B of FIG. 5.
Figure 8:
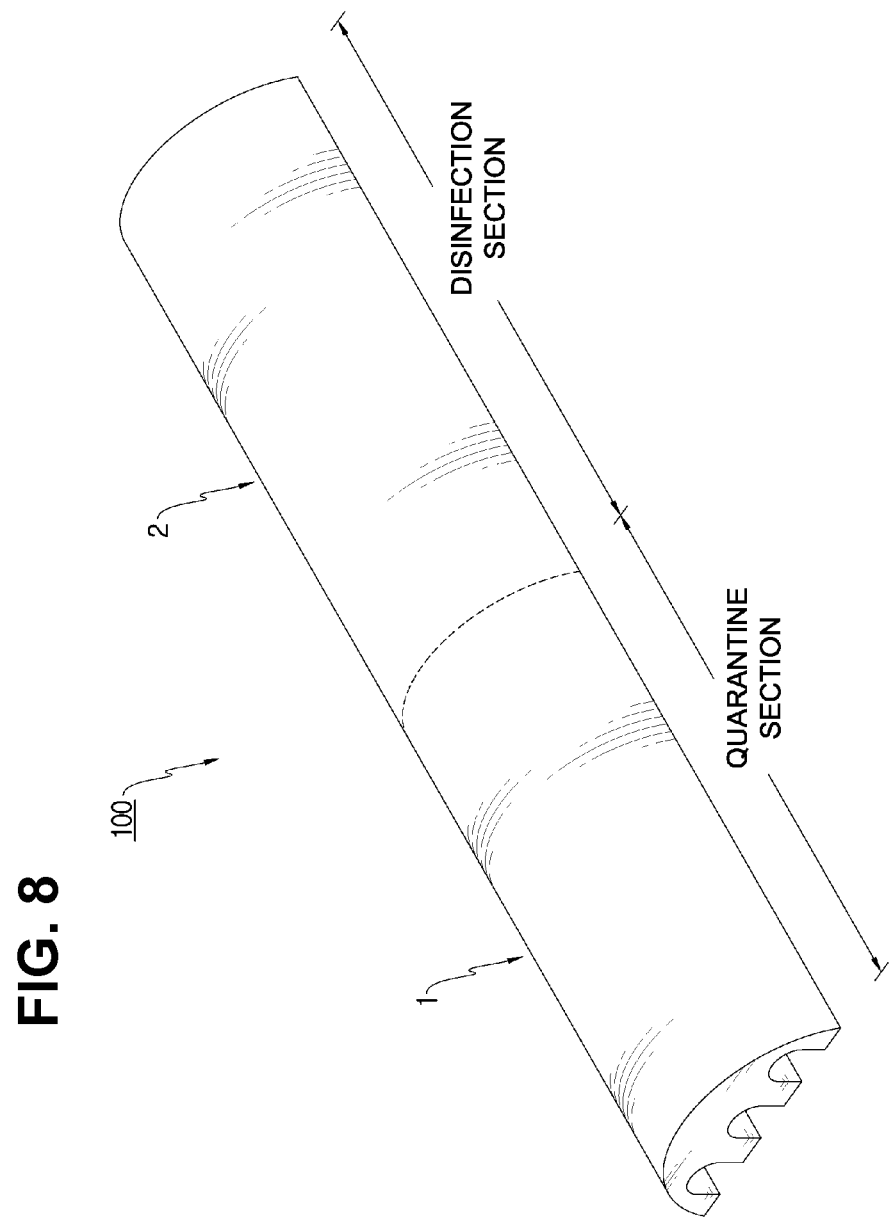
FIG. 8 is a schematic perspective view showing a smart tunnel according to another embodiment of the present disclosure.
Figure 9:
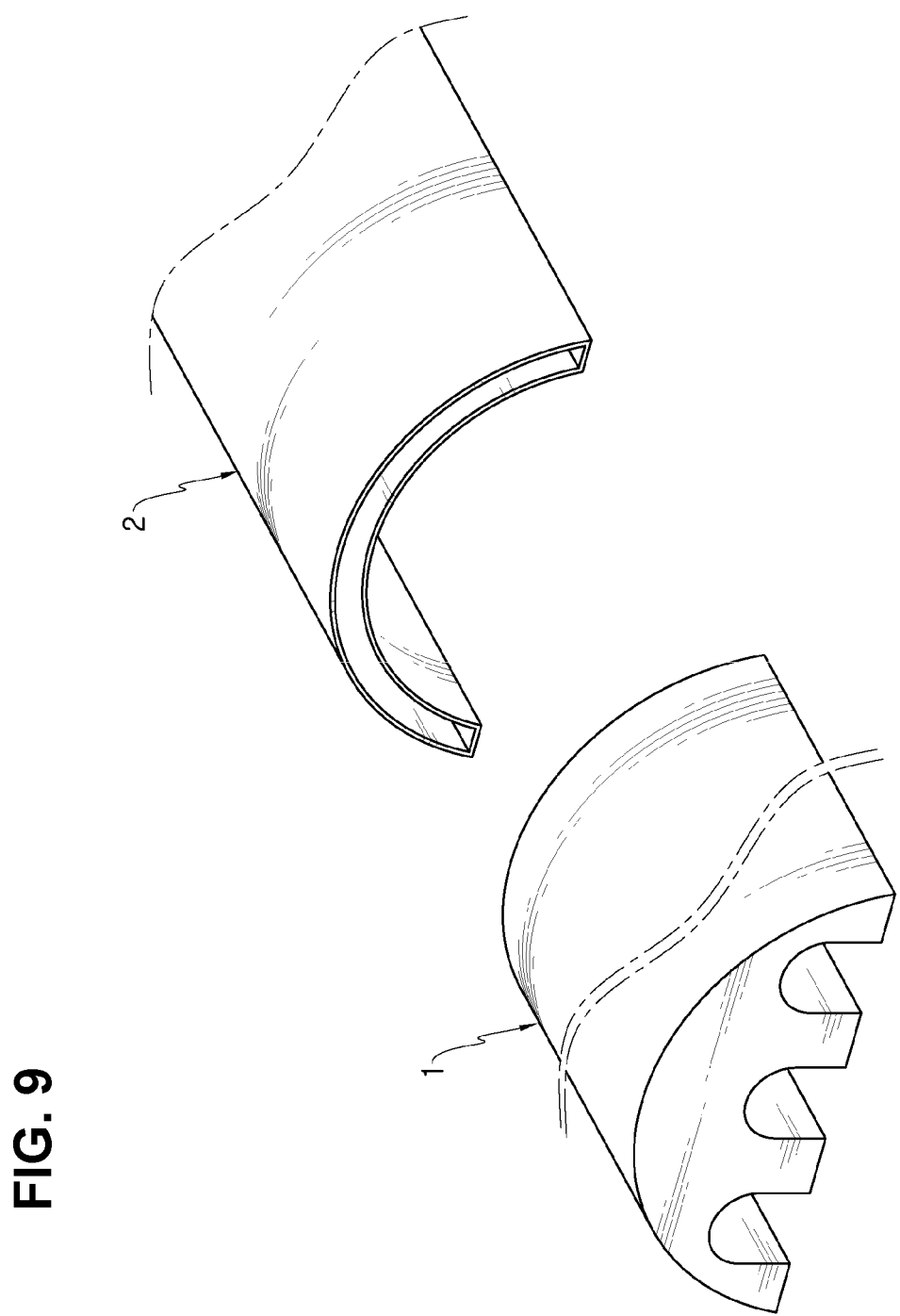
FIGS. 9 and 10 are schematic perspective views showing that a <quarantine section> and a <disinfection section> of the smart tunnel of the present disclosure depicted in FIG. 8 are in a separated state.
Figure 10:
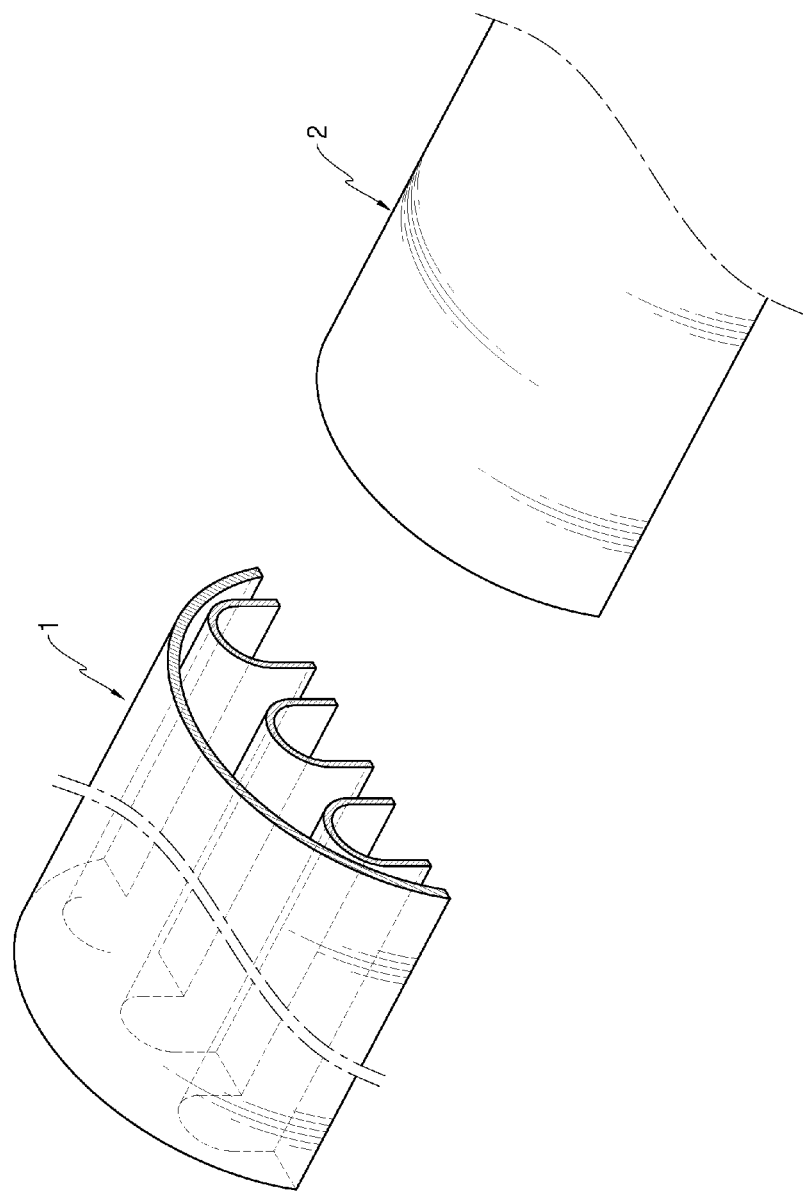

In the embodiment shown in FIGS. 1 to 3, the quarantine section tunnel module 1 is configured as a tunnel structure in which a passageway is formed. In the embodiment of FIGS. 1 to 3, a quarantine section is formed by installing a plurality of tunnel structures in parallel and adjacent to each other. FIG. 4 is a schematic perspective view showing an embodiment of the tunnel structure forming the quarantine section tunnel module 1 in the smart tunnel 100 shown in FIG. 1. FIG. 5 is a schematic longitudinal sectional view showing the quarantine section tunnel module 1, taken along the arrow C-C of FIG. 4. FIG. 6 is a schematic lateral half-sectional perspective view, taken along the arrow A-A of FIG. 5. FIG. 7 is a schematic lateral half-sectional perspective view showing a side opposite to that of FIG. 6, taken along the arrow B-B of FIG. 5.

The intelligent infected person regular detection system includes a thermal imaging camera 10, a visible light camera 11, and a reading control device (not shown in the drawings). The thermal imaging camera 10 and the visible light camera 11 are installed inside the tunnel structure of each of the plurality of quarantine section tunnel modules 1. The thermal imaging camera 10 and the visible light camera 11 photograph a passenger to obtain a thermal image and a visible light image of the passenger, respectively. The obtained image is sent to the reading control device connected to the thermal imaging camera and the visible light camera by wire or wireless, and analyzed to sense and detect an abnormal state (fever, etc.) and an abnormal behavior (cough, collapse, abnormal walking, etc.) of the passenger. By using the analysis result of the obtained image, an infection-suspected person suspected as having an infectious disease is found out, and the face of the identified infection-suspected person is recognized and detected. Specifically, the reading control device finds out a passenger exhibiting an abnormal state or an abnormal behavior as an infection-suspected person from the obtained thermal image and visible light image. The reading control device extracts and obtains a face image of the found-out infection-suspected person. The reading control device transmits the obtained face image of the infection-suspected person to the "infected person integrated control system". In this case, if necessary, it is also possible to transmit other necessary images of the infection-suspected person (the thermal image and the visible light image photographed for the infection-suspected person) along with the face image of the infection-suspected person.

For more thorough quarantine and disinfection for an infectious disease, in order to manage "a person or crowd exposed to infection risk through direct or indirect routes by sharing the same time and space as the infection-suspected person" (an infection-suspected candidate group), the "intelligent infected person regular detection system" may also extract and obtain face images of an infection-suspected candidate group and transmit the face images to the infected person integrated control system.

In the "infected person integrated control system", the "intelligent infected person regular detection system" collects and stores information obtained by and transmitted from each of the plurality of quarantine section tunnel modules 1. The "infected person integrated control system" obtains the identity information (information such as name, address, etc.) of the infection-suspected person, and provides the presence of the infection-suspected person, the identity information of the corresponding infection-suspected person, and other relevant information related to the infection-suspected person (abnormal state and behavior information, face information, etc.) to the manager in real time for alarming and notification. The "infected person integrated control system" includes a data receiving and storing unit that collects and stores the received information. The "infected person integrated control system" includes an image comparison extraction unit that obtains the identity information of the infection-suspected person by comparing the received face image of the infection-suspected person with data that is secured in advance. The "infected person integrated control system" includes an alarm notification unit that notifies the presence of the infection-suspected person and transmits the obtained identity information of the infection-suspected person to the management terminal of the manager.

The data receiving and storing unit receives the face image of the infection-suspected person and other images of the infection-suspected person (the thermal image and the visible light image photographed for the infection-suspected person) from the "intelligent infected person regular detection system". The data receiving and storing unit classifies, organizes and stores the transmitted thermal image and the transmitted visible light image photographed for the infection-suspected person.

The image comparison extraction unit compares the face image of the infection-suspected person with data of an individual database ("individual DB") that is secured in advance by using a known imaging process or the like to find a person who matches with the infection-suspected person, and extracts identity information of the corresponding person. The information extracted in this way becomes the "identity information of the infection-suspected person". The individual DB used by the image comparison extraction unit may be owned by the manager, or may be owned by an external institution such as a government office.

The alarm notification unit notifies the manager of the presence of the infection-suspected person. The alarm notification unit also transmits the identity information of the infection-suspected person to the management terminal of the manager such as a smartphone, a tablet, or a personal computer. At this time, the alarm notification unit may transmit other related information of the infection-suspected person, such as the face image, the abnormal state information and the abnormal behavior information of the infection-suspected person, to the management terminal of the manager along with the identity information of the infection-suspected person. In a "multi-platform supported infected person integrated control system", known devices for transmitting and receiving signals may be used as the data receiving and storing unit and the alarm notification unit. The image comparison extraction unit may be implemented with software running on a computer.

The present disclosure may be configured to perform quarantine management even for an infection-suspected candidate group. In this case, in the "multi-platform supported infected person integrated control system", the face image transmitted from the "intelligent infected person regular detection system" for the infection-suspected candidate group is compared with the individual DB to secure identity information and provide the identity information to the manager.

The "pathogen capturing system" provided in the smart tunnel 100 sucks the air in the quarantine section. The pathogen capturing system captures, separates and concentrates a pathogen contained in the sucked air, namely bacteria and virus, discharged by breathing, cough, etc. of an infected person. The pathogen capturing system determines whether an infectious disease is introduced by checking the type of the separated and concentrated pathogen, and determines what type of infectious disease is introduced. To this end, the "pathogen capturing system" includes a pathogen capturing device 15 installed at the tunnel structure of the quarantine section tunnel module 1. As shown in FIGS. 5 to 7, a capturing inlet 16 is formed at an inner surface of the tunnel structure of each quarantine section tunnel module 1 so that the air in the tunnel structure is sucked to the pathogen capturing device 15. The capturing inlet 16 is in communication with the pathogen capturing device 15.

While an infected person is passing through the quarantine section tunnel module 1, the air in the quarantine section tunnel module 1 is sucked into the pathogen capturing device 15. In the pathogen capturing device 15, the pathogen present in the sucked air is captured, separated and concentrated, and the type of the separated and concentrated pathogen is examined. Based on the examination results, the pathogen capturing device 15 determines what kind of infectious disease is introduced and whether an infectious disease is introduced.

In order to improve the air sucking efficiency to the pathogen capturing device 15, an air injection hole 17 may be formed at an inner surface of the tunnel structure of the quarantine section tunnel module 1. The air injection hole 17 communicates with an air supply device 18. Air may be injected into the tunnel structure through the air supply device 18 and the air injection hole 17. In the embodiment shown in FIG. 5, the capturing inlet 16 in communication with the pathogen capturing device 15 is formed at one side surface of the inside of the tunnel structure. The air injection hole 17 is formed at an opposite side surface of the inside of the tunnel structure, which faces the capturing inlet 16. Air is injected from the air injection hole 17. The air injected from the air injection hole 17 passes by passengers and is sucked into the capturing inlet 16. Therefore, the time required for the pathogen capturing device 15 to suck and capture the pathogen is reduced to increase the sucking and capture efficiency of the pathogen, thereby improving the speed and efficiency in diagnosing whether an infectious disease is introduced. However, if necessary, the air injection hole 17 may not be formed. It is also possible to change the locations of the capturing inlet 16 and the air injection hole 17 to both side surfaces, a ceiling portion, a bottom portion, etc. of the tunnel structure. For example, the air injection hole 17 may be formed at the ceiling portion inside the tunnel structure of the quarantine section tunnel module 1, and the capturing inlet 16 may be formed on one or both side surfaces or the bottom portion of the inside thereof. Also, the air injection hole 17 may be formed at one or both side surfaces of the tunnel structure of the quarantine section tunnel module 1, and the capturing inlet 16 may be formed at an opposite side surface or the bottom portion of the inside, opposite thereto.

The tunnel structure according to the embodiment shown in FIGS. 4 to 7 has a double tunnel type, which includes a plurality of internal tunnel structures 12 and an external tunnel structure 13 provided out of the plurality of internal tunnel structures 12 to surround the plurality of internal tunnel structures 12 entirely at a predetermined interval therefrom. In the tunnel structure a double tunnel type, the pathogen capturing device 15, the air supply device 18, and a pipe communicating the pathogen capturing device 15 and the air supply device 18 may be disposed in the space between the internal tunnel structure 12 and the external tunnel structure 13. Therefore, various equipment necessary for the <quarantine section> may be efficiently arranged in the tunnel structure. Even though the air supply device 18 is shown to have a pipe shape for convenience, the shape of the air supply device 18 may be different therefrom.

In the smart tunnel 100, the <disinfection section> is formed in succession to the <quarantine section> to the exit. The <disinfection section> includes a disinfection section tunnel module 2 configured in a tunnel structure having one tunnel space. The disinfection section tunnel module 2 has a space where passengers having passed through the <quarantine section> pass together. The inlet of the disinfection section tunnel module 2 is connected to the outlet of the quarantine section tunnel module 1. Therefore, passengers who have individually passed through each quarantine section tunnel module 1 pass through the <disinfection section> together in the disinfection section tunnel module 2. In forming the <disinfection section>, if necessary, a plurality of disinfection section tunnel modules 2 may be provided so that each disinfection section tunnel module 2 is connected to the quarantine section tunnel module 1.

In the <disinfection section>, in order to suppress the spread of an infectious disease, "regular quarantine work" for sterilizing and purifying pathogen (bacteria, viruses, etc.) that may exist at the tunnel structure, facilities, and air is performed. For members and facilities in the tunnel structure of the disinfection section tunnel module 2, a finishing material having antibacterial and antiviral performance applied to the surface thereof. An air conditioning system having antibacterial and antiviral performance is installed at the disinfection section tunnel module 2. With this configuration, a pathogen (bacteria, virus, etc.) discharged into the air from an infected person is killed when contacting the finishing material applied in the tunnel structure of the disinfection section tunnel module 2 or passing through the air conditioning system provided at the disinfection section tunnel module 2, thereby achieving regular quarantine. Therefore, even if a passenger who is not an infected person unintentionally passes through the smart tunnel at the same time as the infected person and is exposed to infection risk through direct or indirect routes, the risk of infection by the infectious disease may be reduced. In addition, it is possible to effectively prevent and suppress the transmission and spread of the infectious disease.

An air curtain may be installed between the quarantine section tunnel module 1 and the disinfection section tunnel module 2 so that the <quarantine section> and the <disinfection section> may be more clearly distinguished.

In the embodiment of the drawings, the tunnel structures of the quarantine section tunnel module 1 and the disinfection section tunnel module 2 have a rectangular longitudinal sectional shape and a linearly elongated shape, but the shape is not limited thereto. FIG. 8 is a schematic perspective view of another embodiment of the smart tunnel 100 according to the present disclosure, and FIGS. 9 and 10 are schematic perspective views respectively showing the smart tunnel 100 according to the present disclosure shown in FIG. 8 in which the <quarantine section> and the <disinfection section> are separated. As shown in FIGS. 8 to 10, in the smart tunnel 100, the internal tunnel structure 12 of the quarantine section tunnel module 1 may have an elliptical sectional shape in a longitudinal direction. The <quarantine section> may be formed in a double tunnel type in which an external tunnel structure having one elliptical longitudinal sectional shape surrounds the plurality of internal tunnel structures 12 having an elliptical sectional shape entirely at a predetermined interval. In this case, the disinfection section tunnel module 2 may be installed in succession to have an elliptical sectional shape in accordance with the elliptical sectional shape of the external tunnel structure. In the present disclosure, the longitudinal sectional shape of each of the quarantine section tunnel module 1 and the disinfection section tunnel module 2 may be changed into various shapes, including rectangles and ellipses. The linear shape of the smart tunnel may also be changed into various shapes such as a curved shape as well as a linear shape in consideration of passenger moving lines at the installation location.

The smart tunnel 100 of the present disclosure may be movably installed at immigration facilities such as airports and ports, through which an abroad infectious disease may be introduced, and crowded facilities such as hospitals where active management is required for blocking the introduction of infectious disease and preventing the spread. The smart tunnel 100 of the present disclosure is configured to be capable of controlling a moving line of an infection-suspected person or an infection-suspected group by using the shape characteristics of the tunnel structure. In particular, in the quarantine section tunnel module 1 of the smart tunnel 100, it is possible to rapidly detect whether a person passing through the tunnel is infected with an infectious disease and whether an infectious disease is introduced into any facility or area while the passenger is passing through the tunnel structure. In addition, in the quarantine section tunnel module 1, a regular quarantine that enables an initial response to prevent secondary the spread of infectious diseases is performed by managing the identity information of not only the infected person but also the infection-suspected candidate group in direct or indirect contact with the infected person.

By means of the finishing material and the air conditioning system having antibacterial and antiviral performance and provided to the disinfection section tunnel module 2 of the smart tunnel 100, it is possible to perform regular quarantine against pathogen (bacteria, viruses, etc.) discharged from an infected person into the air.

The present disclosure may be used for establishing a regular quarantine and disinfection system to prevent the spread of infectious diseases in facilities such as airports, ports and hospitals. According to the present disclosure, it is possible to prevent public safety risks, social unrest and economic losses, caused by the introduction and the spread of abroad infectious diseases. The present disclosure may be used as a core technology for building a national safety net related to infectious diseases.

What is claimed is:

1. A smart tunnel, comprising:
 a quarantine section having a plurality of quarantine section tunnel modules configured in a tunnel structure through which one passenger passes and a disinfection section having a disinfection section tunnel module connected to all or a part of the plurality of quarantine section tunnel modules so that passengers passing through the quarantine section pass together are formed sequentially along a moving line of the passengers,
 an intelligent infected person regular detection system for sensing and detecting an abnormal state and an abnormal behavior of each passenger from a thermal image and a visible light image of the passenger passing through each of the plurality of quarantine section tunnel modules to find out an infection-suspected person and obtaining a face image of the infection-suspected person is provided,
 an infected person integrated control system for securing identity information of the infection-suspected person whose face image is obtained and transmitting the presence of the infection-suspected person, the identity information of the infection-suspected person, and the abnormal state information, the abnormal behavior information and the face information of the infection-suspected person received from the intelligent infected person regular detection system to a manager is provided,
 a pathogen capturing system for determining whether an infectious disease is introduced by sucking the air inside the tunnel structure of each of the plurality of quarantine section tunnel modules to capture a pathogen discharged to the air from an infected person and determining the type of the infectious disease is provided,
 wherein the intelligent infected person regular detection system considers a person or crowd exposed to the infection risk by sharing the same time and space as the infection-suspected person as an infection-suspected candidate group, obtains a face image of the infection-suspected candidate group, and transmits the face image of the infection-suspected candidate group to the infected person integrated control system,
 wherein the infected person integrated control system includes a data receiving and storing unit for collecting and storing the received information, an image comparison extraction unit for comparing the received face image of the infection-suspected person and the infection-suspected candidate group with data secured in advance to find a matched person and considering the found corresponding person as the infection-suspected person and the infection-suspected candidate group to obtain identity information of the corresponding infection-suspected person and the corresponding infection-suspected candidate group, and an alarm notification unit for notifying the presence of the infection-suspected person and transmitting the obtained identity information of the infection-suspected person and the infection-suspected candidate group to a management terminal of a manager,
 wherein members and facilities in the tunnel structure of the disinfection section tunnel module are made of a finishing material having antibacterial and antiviral performance,
 wherein an air conditioning system having antibacterial and antiviral performance is provided to the disinfection section tunnel module so that the disinfection section tunnel module performs regular disinfection as a pathogen discharged to the air from an infected person passing through the tunnel structure is killed when contacting the finishing material having antibacterial and antiviral performance or passing through the air conditioning system having antibacterial and antiviral performance;
 wherein the pathogen capturing system includes:
 a pathogen capturing device configured to suck the air in the quarantine section tunnel module through a capturing inlet formed at an inner surface of the tunnel structure of the quarantine section tunnel module while an infected person is passing through the quarantine section tunnel module, capture an pathogen present in the sucked air to be separated and concentrated, check the type of the pathogen to determine whether an infectious disease is introduced, and determine the type of the introduced infectious disease; and
 an air supply device configured to inject the air into the quarantine section tunnel module through an air injection hole formed at the inner surface of the tunnel structure of the quarantine section tunnel module,
 wherein the tunnel structure of the quarantine section tunnel module has a double tunnel type including a plurality of internal tunnel structures and an external tunnel structure provided out of the plurality of internal tunnel structures to surround the plurality of internal tunnel structures entirely at an interval therefrom, and
 wherein the pathogen capturing device and the air supply device are disposed in the space between the internal tunnel structure and the external tunnel structure.

2. The smart tunnel according to claim 1,
 wherein the intelligent infected person regular detection system includes:
 a thermal imaging camera installed in the tunnel structure of each of the plurality of quarantine section tunnel modules to obtain a thermal image of a passenger;

a visible light camera installed in the tunnel structure of each of the plurality of quarantine section tunnel modules to obtain a visible light image of the passenger; and a reading control device configured to find out a passenger exhibiting an abnormal state or an abnormal behavior in the obtained thermal image and visible light image of the passenger as an infection-suspected person and extract and obtain a face image of the found-out infection-suspected person.

3. The smart tunnel according to claim 1, wherein the capturing inlet is formed at one side surface of the inside of the tunnel structure of the quarantine section tunnel module, wherein the air injection hole is formed at a side surface of the inside of the tunnel structure of the quarantine section tunnel module, which is opposite to the side surface at which the capturing inlet is formed, and wherein the air injected from the air injection hole is provided to pass by the passenger and flow to the capturing inlet.

4. The smart tunnel according to claim 1, wherein the capturing inlet is formed at a side surface of the inside of the tunnel structure of the quarantine section tunnel module, wherein the air injection hole is formed at a ceiling portion of the inside of the tunnel structure of the quarantine section tunnel module, and wherein the air injected from the air injection hole is provided to pass by the passenger and flow to the capturing inlet.

5. The smart tunnel according to claim 1, wherein the capturing inlet is formed at a bottom portion of the inside of the tunnel structure of the quarantine section tunnel module, wherein the air injection hole is formed at a side surface of the inside of the tunnel structure of the quarantine section tunnel module, and wherein the air injected from the air injection hole is provided to pass by the passenger and flow to the capturing inlet.

* * * * *